United States Patent [19]

Stefani et al.

[11] 4,100,106

[45] Jul. 11, 1978

[54] PROCESS FOR THE PRODUCTION OF A MIXED-OXIDE OXIDATION CATALYST CONTAINING VANADIUM AND PENTAVALENT PHOSPHORUS

[75] Inventors: Giancarlo Stefani, Bergamo, Italy; Pietro Fontana, Schaffhausen, Switzerland

[73] Assignee: Lonza, Ltd., Basel, Switzerland

[21] Appl. No.: 648,025

[22] Filed: Jan. 12, 1976

[30] Foreign Application Priority Data

Jan. 10, 1975 [CH] Switzerland .................. 00266/75

[51] Int. Cl.$^2$ ............................................. B01J 27/14
[52] U.S. Cl. ..................................... 252/437; 252/435
[58] Field of Search ................................. 252/435, 437

[56] References Cited

U.S. PATENT DOCUMENTS

| B 330,354 | 1/1975 | Mount et al. | 252/435 X |
|---|---|---|---|
| 3,156,705 | 11/1964 | Kerr | 252/435 X |
| 3,156,707 | 11/1964 | Kerr | 252/435 X |
| 3,255,212 | 6/1966 | Kerr | 252/435 X |
| 3,538,122 | 11/1970 | Friedrichsen et al. | 252/435 X |
| 3,684,741 | 8/1972 | Friedrichsen et al. | 252/435 |
| 3,888,886 | 6/1975 | Young et al. | 252/437 X |
| 3,977,998 | 8/1976 | Freerks et al. | 252/435 |

FOREIGN PATENT DOCUMENTS

| 2,256,909 | 5/1973 | Fed. Rep. of Germany. |
|---|---|---|
| 2,354,872 | 5/1974 | Fed. Rep. of Germany. |
| 2,328,755 | 1/1974 | Fed. Rep. of Germany. |

*Primary Examiner*—Patrick P. Garvin
*Assistant Examiner*—William G. Wright
*Attorney, Agent, or Firm*—Virgil H. Marsh

[57] ABSTRACT

The process for the production of a mixed-oxide oxidation catalyst which, based on the vanadium and pentavalent phosphorus, has an atomic ratio of phosphorus to vanadium between 1.05 to 1 and 1.10 to 1. The process involves reacting a salt of tetravalent vanadium, dissolved in a non-oxidizing acid aqueous solution, with orthophosphoric acid. The resultant soluble vanadium salt complex, after concentrating the solution is precipitated by adding water. The precipitate is dried. The dried precipitate is put or formed into the desired form. The formed, dried precipitate is subjected to a heat treatment of at least 300° C. A mixed-oxide oxidation catalyst is obtained.

18 Claims, No Drawings

PROCESS FOR THE PRODUCTION OF A MIXED-OXIDE OXIDATION CATALYST CONTAINING VANADIUM AND PENTAVALENT PHOSPHORUS

BACKGROUND OF THIS INVENTION

1. Field of This Invention

The invention relates to a process for the production of a mixed-oxide oxidation catalyst, which, on the basis of vanadium and pentavalent phosphorus, has an atomic ratio of phosphorus to vanadium between 1.05 to 1 and 1.10 to 1, and to a process for the use of the mixed-oxide obtained according to the process as a catalyst for the production of maleic anhydride from $C_4$-hydrocarbons of a saturated or unsaturated kind.

2. Prior Art

The production of vanadium-phosphorus mixed oxides and their use as oxidation catalysts is known. German Published Application No. 2,256,909 describes the production of a vanadium-phosphorus mixed oxide catalyst, having an atomic ratio of phosphorus to vanadium of 1:1 to 2:1, by the complete concentration of a solution of a pentavalent phosphorus compound and a vanadium compound in concentrated aqueous hydrochloric acid and subsequent formation with the help of a complicated multistep heat treatment. The exact control of the heat treatment process with regard to temperature, duration in time and atmosphere of the surroundings is given as the prerequisite for achieving sufficient catalytic activity of the resulting dehydrated mixed oxide. In the case of the technical and commercial production of catalysts, it is however exceedingly difficult and expensive to maintain (keep within) such complicated conditions as the process of such German published application.

German Published Application No. 2,328,755 describes the production of an oxidation catalyst having a high specific surface and a special crystallic structure, which is designated as $\beta$-phase and is defined by its x-ray difraction spectrum. At the same time the preliminary catalyst product, that is to say the uncalcined catalyst, is obtained by heating and completely concentrating a practically anhydrous hydrochloric acid solution of an approximately tetravalent vanadium compound and a 100 percent phosphoric acid. Water can only be present in small quantities, whenever the active mixed oxide described by the German published application is to be obtained. For such formation, again a complicated multistep heat treatment, analogous to the previously mentioned German published application, is necessary. Beside the already discussed disadvantage of the demanding heat treatment, the necessity of the use of organic solvents is disadvantageous.

The $C_4$-hydrocarbons, especially n-butane, owing to their considerably lower price, are economically superior to benzene which at the present day is customarily used for the large-scale industrial production of maleic anhydride.

In the case of the mixed-oxide catalysts obtained according to the two above-mentioned German publications, quite high yields are achieved in oxidation of n-butane to maleic anhydride. The specific throughputs of n-butane used in such case, however, are far below those customarily obtained in industry and required for a reasonably profitable commercial process.

The additional known processes of the prior art either use only very small turnovers and return the unreacted starting material into the process, which is conditional on the supply (feeding in) of pure oxygen to the reaction mixture (for example, German Published Application No. 2,354,872), or else they require temperatures of above 500° C. in order to achieve mere moderate yields, a factor which considerably reduces the useful life of the catalyst.

BROAD DESCRIPTION OF THIS INVENTION

An object of this invention is to provide a process for the production of a mixed-oxide oxidation catalyst containing vanadium and pentavalent phosphorus. Another object of this invention is to provide such a production process that is uncomplicated and can be conducted on a commercial or industrial scale. Another object of this invention is to provide a process of using such mixed-oxide oxidation catalyst to produce maleic anhydride from $C_4$-hydrocarbons. A further object of this invention is to provide such a mixed-oxide oxidation catalyst. Other objects and advantages of this invention are set out herein or are obvious herefrom to one ordinarily skilled in the art.

The objects and advantages of this invention are achieved by the processes and product of this invention.

This process involves a process for the production of a mixed-oxide oxidation catalyst which, based on the vanadium and pentavalent phosphorus, has an atomic ratio of phosphorus to vanadium between 1.05 to 1 and 1.10 to 1. The process includes reacting a salt of the tetravalent vanadium, dissolved in a non-oxidizing acid aqueous solution, with orthophosphoric acid. The resultant soluble vanadium salt complex is precipitated by adding water. The precipitate is dried. The dried precipitate is formed or put into the desired form. The formed, dried precipitate is subjected to a heat treatment of at least 300° C. A mixed-oxide oxidation catalyst is obtained.

An advantage of this production process is that it does not need to use an organic solvent. Another advantage of this invention is that it provides an uncomplicated process which can easily be carried out on a commercial or industrial scale.

This invention also involves the catalyst produced by the catalyst production process of this invention. The catalyst of this invention can operate at relatively low temperatures with high yields and selectivity, has a long useful life and which permits economical operation with high hydrocarbon through-puts. The catalyst has uniformly good characteristics, i.e., is uniform in its properties.

The catalyst produced by the production process of this invention can be used to produce maleic anhydride from saturated or unsaturated $C_4$-hydrocarbons. Examples of such $C_4$-hydrocarbon starting materials are n-butane (preferred), isobutane, 1,2-butadiene, 1,3-butadiene, 1-butene, 2-butene, isobutylene and 2-butyne.

This invention further includes the process of using the mixed-oxide oxidation catalyst, obtained by the production process of this invention, as an oxidation catalyst in the production of maleic anhydride from $C_4$-hydrocarbons in the gaseous phase.

Advantages of this catalyst-usage process include that it has a high hydrocarbon through-put, provides economical operation, can be operated at relatively low temperatures with high yields and selectivity and can be used on an industrial scale.

DETAILED DESCRIPTION OF THIS INVENTION

It is preferable in some cases to add to the mixed-oxide of this invention, on the basis of the vanadium and phosphorus, having an atomic ratio of phosphorus to vanadium between 1.05 to 1 and 1.10 to 1, titanium dioxide as a further component. This can be accomplished before the precipitation of the mixed oxide by adding the titanium dioxide. Preferably, however, the titanium dioxide is added to the mixed oxide precipitate prior to the formation and heat treatment steps. The quantity of titanium dioxide is such that the portion of titanium dioxide in the mixed oxide is up to 20 percent, preferably 1 to 5 percent by weight.

The soluble vanadium phosphorus salt complex is preferably obtained by boiling a vanadium compound in a mixture of concentrated aqueous hydrochloric acid and 85 percent phosphoric acid. This boiling is carried out advantageously over a prolonged period of time, preferably within a period of a few hours, especially whenever the vanadium salt is formed in situ through reduction of a pentavalent vanadium compound. In such case, moreover, it is advantageous to add oxalic acid to the concentrated aqueous hydrochloric acid.

Examples of acids which can be used in the acid solution are the strong acids, such as nitric acid, sulfuric acid and hydrochloric acid (preferred). Examples of acids which can be used in conjunction with the strong acids are oxalic acid (preferred), acetic acid, tartaric acid, formic acid, lactic acid and boric acid. (These non-oxidizing acids do not include orthophosphoric acid.)

Although it is not important which atomic ratio of phosphorus to vanadium exists in the starting solution, since in the precipitation one always obtains the desired atomic ratio of phosphorus to vanadium between 1.05 to 1 and 1.10 to 1, it is preferable to use an atomic ratio of phosphorus to vanadium in the starting solution which amounts to about 1.08 to 1. In the case of this method of operation, the mother lye obtained after separation of the vanadium-phosphorus salt complex is concentrated, reconcentrated and used again.

The tetravalent vanadium, which is used as a starting product in the solution, can be obtained either by the use of a tetravalent vanadium salt or else by the use of an easily accessible pentavalent vanadium compound, such as vanadium pentoxide, is reduced in situ to a tetravalent vanadium salt. Examples of useful soluble tetravalent vanadium salts are: vanadium tetrachloride ($VCl_4$); vanadium dioxide ($VO_2$), sometimes termed vanadium tetraoxide ($V_2O_4$); vanadium oxydibromide ($VOB_{R2}$); vanadium oxydichloride ($VOCl_2$); and vanadyl sulfate ($VOSO_4$). In general, the useful soluble tetravalent vanadium salts are halides, oxides and oxyhalides of vanadium.

Examples of useful pentavalent vanadium compounds, which can be reduced in situ to obtain a soluble tetravalent vanadium salt, are: vanadium pentaoxide ($V_2O_5$), which is the preferred compound; vanadium oxytribromide $VOBr_3$); vanadium oxytrichloride ($VOCl_3$); and vanadium pentachloride ($VCl_5$).

As a result of the forming and heat treatment steps, the catalyst is put into a practical form, for example, molded pellets, tablets, extruded cylinders. The heat treatment is carried out at a temperature of at least 300° C., preferably at a temperature of 350° to 650° C., and most preferably at 400° to 550° C. Heat treatment times of 2 to 24 hours, preferably 4 to 12 hours, are used.

The heat treatment can take place in the presence of air. In special cases it is effective to operate under partial or complete exclusion of oxygen, especially whenever the catalyst contains titanium dioxide.

The vanadium-phosphorus complex, which is completely filling, is decisive for the end product. The filling dried at 100° C., i.e., the preliminary step of the catalyst prior to the heat treatment, is a uniform ternary compound of V, P and O with a well-defined crystalline structure which is characterized by the following X-ray difraction spectrum (CuK):

Table I

| D-values (Angström) | Intensity | d-values (Angström) | Intensity |
|---|---|---|---|
| 5.83 | SS | 2.65 | S |
| 5.65 | ST | 2.60 | S |
| 4.79 | S | 2.55 | SSS |
| 4.53 | ST | 2.44 | SSS |
| 4.08 | S | 2.39 | S |
| 3.68 | M | 2.25 | SSS |
| 3.29 | M | 2.22 | S |
| 3.10 | M | 2.20 | SSS |
| 2.95 | SSS | 2.12 | SS |
| 2.94 | ST | 2.10 | SSS |
| 2.78 | M | 2.04 | SS |

Beside the lines mentioned, which correspond to a single structural type which is not registered in the ASTM card file, no reflexes of simple oxides of the two metals are visible. This proves that it cannot be a matter of a mere mixture of oxides.

The oxidation catalyst obtained by the process of this invention is well suited for the production of maleic anhydride by oxidation of n-butane in the gaseous phase. For this purpose, such catalysts which contain titanium dioxide, preferably in quantities of 1 to 5 percent by weight, are particularly preferred. The oxidation can be carried out with a mixture of oxygen and any inert gas (e.g., nitrogen, argon, etc.) desired. Preferably air is used in a weight ratio of 15:1 to 35:1, preferably 27:1 to 33:1, related to the n-butane feed. For the oxidation of the n-butane peak, a reaction temperature of 320° to 500° C., preferably 360° to 460° C., is used.

As compared to the known catalysts which show good yields only in the case of industrially uninteresting throughputs of a maximum of about 40 gm of butane per hour per liter of catalyst, using the catalyst according to this invention one can obtain high yields at industrial butane through-puts of 80 to 100 gm per hour, or more, per liter of catalyst.

As a result of the fact that according to the process of this invention a mixed oxide is always obtained having an atomic ratio of phosphorus to vanadium of about 1.08 to 1, industrial production presents no problems.

Furthermore, isolation of the catalyst-preliminary product through filtration is technologically simpler to handle than the production through complete evaporation of the concentrated acid solution as required in accordance with the prior art processes.

A great advantage of the catalyst-preliminary product obtained according to the process of this invention is the excellent reproducibility of the chemical and physical characteristics. The consequence of this characteristic of the preliminary product is that the heat treated material, i.e., the finished catalyst, produces completely reproducible results and retains its high activities practically unchanged for several months.

To repeat, this invention converts (reacts) a salt of tetravalent vanadium, dissolved in a non-oxidizing acid, acid aqueous solution, with orthophosphoric acid into a soluble vanadium phosphorus complex salt. The complex salt is precipitated by the addition of water. The precipitate is dried and is subjected to a heat treatment of at least 300° C. The process of this invention is a simple process which can be carried out on an industrial scale for the production of a vanadium-phosphorus mixed-oxide catalyst. The catalyst has uniformly good characteristics and is useful for the oxidation of hydrocarbons (saturated or unsaturated), having carbon, especially for the oxidation of n-butane, into maleic anhydride. The catalyst is useful for the large-scale industrial conversion of n-butane into maleic anhydride, can operate at relatively low temperatures with a high yield and selectivity, has a long, useful life and permits economical operation with high hydrocarbon through-puts.

Herein all parts, percentages and proportions are expressed on a weight basis, unless otherwise obvious to one ordinarily skilled in the art.

EXAMPLE 1

1000 gm of $V_2O_5$ was suspended in 8000 gm of 36 percent HCl (aqueous solution). The suspension was heated carefully, while stirring, to 100° C. and was boiled for 2 hours under reflux. Then 70 gm of anhydrous oxalic acid, dissolved in 700 ml of water, was added slowly, and finally 1370 gm of 85 percent $H_3PO_4$ was added. This admixture was concentrated to a volume of about 2000 ml, and then 2000 ml of water was added to the viscous solution obtained in that way. A bright blue crystalline precipitate was obtained. The precipitate was filtered out and boiled with water. The mother lye was kept for an additional charge. The atomic ratio of phosphorus to vanadium (P/V) in the filter residue was 1.08 to 1. This solid body (i.e., filter residue) was dried at 100° C., shaped into cylinders and then heated in the presence of nitrogen and small quantities of oxygen (until calcination) for 6 hours at 550° C. Thus, a mixed-oxide oxidation catalyst suitable for use in a solid bed was obtained.

EXAMPLE 2

1000 gm of $V_2O_5$ was suspended in 8000 gm of 37 percent HCl (aqueous solution). The suspension was heated slowly to 100° C. while stirring and was boiled for 2 hours under reflux. 70 gm of anhydrous oxalic acid, dissolved in 700 g of water, was slowly added and subsequently 1370 gm of 85 percent $H_3PO_4$ was added. The solution was completely concentrated, as a result of which a bluish-green solid body was obtained. The solid body was dried at 100° C. until it was constant in weight. The dry material was ground, molded into cylinders and calcined as in Example 1. A mixed-oxide oxidation catalyst suitable for use in a solid bed was obtained.

EXAMPLE 3

A V-P-O mixed-oxide filling was produced as in Example 1—the atomic ratio of P/V likewise was 1.08 to 1. Drying was carried out at 100° C., but the process was stopped at that point. An aqueous solution of $TiCl_4$ was prepared and reacted while stirring with an aqueous ammonia until a pH of 10 was reached. The resultant precipitate thereby was filtered out and washed with water. The resultant filter residue (a $TiO_2$ paste) contained up to about 20 percent $TiO_2$ and up to 80 percent water. 1000 gm of the above-described V-P-O complex (filling) was mixed with 150 gm of the $TiO_2$ paste (corresponding to 30 gm $TiO_2$). The admixture was shaped into cylinders. The cylinders were dried in the air at 100° C. and were then kept at 450° C. for 6 hours in a stream of nitrogen. A mixed-oxide oxidation catalyst suitable for use in a solid bed was obtained.

EXAMPLE 4

Exactly as in Example 1, a V-P-O mixed oxide complex was precipitated, isolated and dried at 100° C. The P/V atomic ratio was 1.08 to 1. 1000 gm of the dry V-P-O complx was mixed with 30 gm of $TiO_2$ and the mixture was made into a paste by the addition of water. The paste was shaped into cylinders. The cylinders were dried in air at 100° C. and then were finally dried (calcined) at 450° C., while flushing in nitrogen, for 6 hours. A mixed-oxide oxidation catalyst suitable for use in the solid bed was obtained.

EXAMPLES 5 TO 19

The catalysts of Examples 1 to 4 were examined for their behavior (and the results they produced) in the case of the catalytic oxidation of various $C_4$-hydrocarbons, especially of n-butane, through air. The conditions in each example are given in Table II. The contact time was varied between the various examples. A steel pipe of 25 mm diameter and approximately 5 m length served as the reactor. The steel pipe always contained at least 1 kg of catalyst filling. Salt melts were used as the heat transfer agents.

The results of the various examples are summarized in Table II. In Table II, the temperature data for the salt bath and hot spot always refer to the temperatures at which the highest yield is of maleic anhydride (related to $C_4$-hydrocarbons used) were obtained. The duration of each of Examples 5 to 19 was several months without interruption, during which the yields remained practically constant. The lowest yield obtained of maleic anhydride was 80 weight percent.

Table II

| Example No. | Catalyst of Example No. | Volume Rate, $h^{-1}$ | Contact Time, Sec. | $C_4$-hydrocarbon | Catalyst Charging, g/h / 1 cat. | Weight Ratio, Air to Butane | Salt Bath Temp., ° C. | Hot Spot Temp., ° C. | Yield of Maleic Anhydride, Weight Percent |
|---|---|---|---|---|---|---|---|---|---|
| 5 | 1 | 1800 | 0.5 | n-butane | 80 | 30 | 420 | 460 | 90 |
| 6 | 1 | 820 | 1.0 | n-butane | 40 | 30 | 400 | 435 | 98 |
| 7 | 1 | 390 | 2.0 | n-butane | 20 | 30 | 370 | 400 | 103 |
| 8 | 2 | 1690 | 0.5 | n-butane | 80 | 30 | 460 | 505 | 80 |
| 9 | 2 | 790 | 1.0 | n-butane | 40 | 30 | 420 | 460 | 92 |
| 10 | 2 | 380 | 2.0 | n-butane | 20 | 30 | 380 | 415 | 99 |
| 11 | 3 | 1900 | 0.5 | n-butane | 80 | 30 | 380 | 420 | 89 |
| 12 | 3 | 880 | 1.0 | n-butane | 40 | 30 | 350 | 380 | 95 |
| 13 | 3 | 420 | 2.0 | n-butane | 20 | 30 | 330 | 350 | 98 |
| 14 | 4 | 1880 | 0.5 | n-butane | 80 | 30 | 385 | 425 | 87 |
| 15 | 1 | 1830 | 0.5 | 1-butene | 80 | 30 | 400 | 445 | 105 |
| 16 | 3 | 1910 | 0.5 | 1-butene | 80 | 30 | 370 | 420 | 103 |

Table II-continued

| Example No. | Catalyst of Example No. | Volume Rate, $h^{-1}$ | Contact Time, Sec. | $C_4$-hydrocarbon | Catalyst Charging, g/h / 1 cat. | Weight Ratio, Air to Butane | Salt Bath Temp., °C. | Hot Spot Temp., °C. | Yield of Maleic Anhydride, Weight Percent |
|---|---|---|---|---|---|---|---|---|---|
| 17 | 3 | 1950 | 0.5 | butadiene | 80 | 30 | 360 | 410 | 110 |
| 18 | 3 | 2860 | 0.35 | n-butane | 114 | 30 | 390 | 440 | 85 |
| 19 | 3 | 2820 | 0.35 | n-butane | 137 | 25 | 390 | 455 | 80 |

What is claimed is:

1. The process for the production of a mixed-oxide oxidation catalyst, which, based on the vanadium and pentavalent phosphorus, has an atomic ratio of phosphorus to vanadium between 1.05 to 1 and 1.10 to 1, by reacting a salt of the tetravalent vanadium, dissolved in a concentrated non-oxidizing acid aqueous solution with orthophosphoric acid forming a vanadium-phosphorus-oxide-complex, isolating the complex, putting the dried complex into the desired form and subjecting the formed catalyst material to a heat treatment of at least 300° C., the improvement which comprises the step of isolating the vanadium-phosphorus-oxide-complex by precipitating the complex by adding water to the concentrated solution.

2. The process of claim 1 wherein said precipitated complex is filtered from said water-diluted solution.

3. The process of claim 1 wherein the vanadium phosphorus salt complex is obtained by boiling of the tetravalent vanadium salt in a mixture of concentrated aqueous hydrochloric acid and 85 percent orthophosphoric acid.

4. The process of claim 1 wherein the acid aqueous solution additionally contains oxalic acid.

5. The process of claim 1 wherein the acid aqueous solution is acidified with hydrochloric acid.

6. The process of claim 8 wherein oxalic acid is also present in the acid aqueous solution.

7. The process of claim 1 wherein the atomic ratio of phosphorus to vanadium in the starting solution is about 1.08 to 1.

8. The process of claim 1 wherein the soluble salt of the tetravalent vanadium is obtained by the in situ reduction of a compound of pentavalent vanadium.

9. The process of claim 11 wherein the compound of pentavalent vanadium is vanadium pentaoxide.

10. The process of claim 1 wherein the heat treatment step is conducted at a temperature of 350° to 650° C. for 2 to 24 hours.

11. The process of claim 1 wherein the heat treatment step is conducted at a temperature of 400° to 550° C. for 4 to 12 hours.

12. The process of claim 1 wherein the heat treatment step is conducted in the presence of air.

13. The process of claim 1 wherein the heat treatment step is conducted with at least a partial exclusion of oxygen.

14. The process of claim 1 wherein, during the production process, titanium dioxide is added as a further component, enough titanium dioxide being added so that the portion of titanium dioxide in the mixed-oxide oxidation catalyst is up to 20 percent by weight.

15. The process of Claim 1 wherein, during the catalyst production process, titanium dioxide is added as a further component to the dried precipitate before the heat treatment step, enough titanium dioxide being added so that the portion of titanium dioxide in the mixed-oxide oxidation catalyst is up to 20 percent by weight.

16. The process of Claim 15 wherein the titanium dioxide and the dried precipitate were made into a paste by the addition of water.

17. The process of Claim 15 wherein the titanium dioxide, in the form of an aqueous paste, is admixed with the dried precipitate.

18. The process of Claim 15 wherein enough titanium dioxide is added so that the portion of titanium dioxide in the mixed-oxide oxidation catalyst is between 1 and 5 percent by weight.

* * * * *